US008615068B2

(12) United States Patent  (10) Patent No.: US 8,615,068 B2
Gunawardena et al.  (45) Date of Patent: Dec. 24, 2013

(54) SYSTEM AND METHOD FOR INTENSITY MODULATED ARC THERAPY TREATMENT PLANNING

(75) Inventors: Athula De Alwis Gunawardena, Fitchburg, WI (US); Michael Charles Ferris, Madison, WI (US); Robert Ricardo Meyer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 298 days.

(21) Appl. No.: 13/242,855

(22) Filed: Sep. 23, 2011

(65) Prior Publication Data

US 2013/0077751 A1 Mar. 28, 2013

(51) Int. Cl.
*A61N 5/10* (2006.01)
(52) U.S. Cl.
USPC ............................. 378/65; 378/145; 378/152
(58) Field of Classification Search
USPC ............. 378/64–65, 145, 147, 149, 150, 151, 378/152
See application file for complete search history.

(56) References Cited

U.S. PATENT DOCUMENTS

| 7,015,490 B2 * | 3/2006 | Wang et al. ................. 250/505.1 |
| 2008/0063141 A1 * | 3/2008 | Luan et al. ........................ 378/65 |

OTHER PUBLICATIONS

Ahuja, et al., A network flow algorithm to minimize beam-on time for unconstrained multileaf collimator problems in cancer radiation therapy, Networks, 2005, 45:36-41.
Alber, et al., Intensity modulated radiotherapy treatment planning by use of a barrier-penalty multiplier method, Optimization Methods and Software, 2007, 22(3):391-411.
Boland, et al., Minimizing beam-on time in cancer radiation treatment using multileaf collimators, Networks, 2004, 43:226-240.
Bortfeld, et al., X-ray field compensation with multileaf collimators, Int. J. Radiat. Oncol. Biol. Phys., 1994, 28:723-730.
Boyer, et al., Intensity-modulated radiation therapy with dynamic multileaf collimators, Semin. Radiat. Oncol., 1999, 9(1):48-59.
Carol, et al., A binary volume delivery system temporal-based intensity modulation radiation therapy, Med. Phys., 1997, 24:996-997.
Chui, et al., Dose calculation for photon beams with intensity modulation generated by dynamic jaw or multileaf collimations, Med. Phys., 1994, 21:1237-1244.
Earl, et al., Inverse planning for intensity-modulated arc therapy using direct aperture optimization, Physics in Medicine and Biology, 2003, 48:1075-1089.

(Continued)

*Primary Examiner* — Hoon Song
(74) *Attorney, Agent, or Firm* — Quarles & Brady, LLP (57) ABSTRACT

A system and method for producing an intensity modulated arc therapy ("IMAT") treatment plan are provided. A plurality of segmentations are generated, from which the IMAT treatment plan is determined. Apertures within each segmentation are ordered by minimizing the total leaf movement between pairs of segmentations in adjacent angles, during which corresponding minimum total leaf movement values between such pairs are calculated. From these segmentations, a network model is used to select those segmentations to be used in the IMAT treatment plan. The apertures in the selected segmentations are then modified by minimizing total leaf movement relative to the selected segmentations, and subject to physical constraints such as a maximum leaf movement constraint or interdigitation constraint. Segmentation errors in the modified segmentations are then locally minimized using a network model and a row-non-convexity measure to determine the order in which apertures are to be optimized.

15 Claims, 5 Drawing Sheets

(56) References Cited

OTHER PUBLICATIONS

Ferris, et al., Sampling issues for optimization in radiotherapy, Annals of Operations Research, 2006, 148:95-116.

Ferris, et al., An optimization approach for radiosurgery treatment planning, SIAM Journal on Optimization, 2003, 13:921-937.

Ferris, et al., Radiation treatment planning: Mixed integer programming formulations and approaches, (Oct. 2002), In G. Appa, L. Pitsoulis, and H. P. Williams, editors, Handbook on Modelling for Discrete Optimization, pp. 317-340. Springer, New York, NY, 2006.

Galvin, et al., Combining multileaf fields to modulate fluence distributions, Int. J. Radiat. Oncol. Biol. Phys., 1993, 27:697-705.

Gunawardena, et al., Discrete approximations to real-valued leaf sequencing problems in radiation therapy, Discrete Applied Mathematics, 2008, 156(17):3178-3186.

Gunawardena, et al., A difference-matrix metaheuristic for intensity map segmentation in step-and-shoot IMRT delivery, Physics in Medicine and Biology, 2006, 51:2517-2536.

Hamacher, et al., Inverse radiation therapy planning—a multiple objective optimization approach, Discrete Applied Mathematics, 2002, 118:145-161.

Holmes, et al., An iterative filtered backprojection inverse treatment planning algorithm for tomotherapy, Int. J. Radiat. Oncol. Biol. Phys., 1995, 32(4):1215-1225.

Li, et al., Monte Carlo dose verification of intensity-modulated arc therapy, Physics in Medicine and Biology, 2001, 46:2269-2282.

Olafsson, et al., Linear programing formulations and algorithms for radiotherapy treatment planning, Optimization Methods and Software, 2006, 21(2):201-231.

Romeijn, et al., A column generation approach to radiation therapy treatment planning using aperture modulation, SIAM Journal on Optimization, 2005, 15(3):838-862.

Romeijn, et al., A new linear programming approach to radiation therapy treatment planning problems, Operations Research, 2006, 54:201-216.

Shepard, et al., Optimizing the delivery of radiation therapy to cancer patients, SIAM Review, 1999, 41:721-744.

Wang, et al., Arc-modulated radiation therapy (AMRT): a single-arc form of intensity-modulated arc therapy, Physics in Medicine and Biology, 2008, 53:6291-6303.

Webb, Optimizing the planning of intensity-modulated radiotherapy, Physics in Medicine and Biology, 1994, 39:2229-2246.

Xia, et al., Multileaf collimator leaf sequencing algorithm for intensity modulated beams with multiple static segments, Medical Physics, 1998, 25:1424-1434.

Yu, Intensity-modulated arc therapy with dynamic multileaf collimation: an alternative to tomotherapy, Physics in Medicine and Biology, 1995, 40:1435-1449.

\* cited by examiner

SYSTEM AND METHOD FOR INTENSITY MODULATED ARC THERAPY TREATMENT PLANNING

STATEMENT REGARDING FEDERALLY SPONSORED RESEARCH

This invention was made with government support under CA130814 awarded by the National Institutes of Health and FA9550-07-1-0389 awarded by the USAF/AFOSR. The government has certain rights in the invention.

BACKGROUND OF THE INVENTION

The field of the invention is systems and methods for radiation therapy. More particularly, the invention relates to systems and methods for designing a radiation treatment plan for a radiation therapy system, such as an intensity modulated arc therapy system ("IMAT").

In practice, intensity modulated radiation therapy ("IMRT") can be delivered in two ways: via a fixed gantry and via a rotatable gantry. Fixed-gantry IMRT is achieved by delivering overlapping fields from a small number of fixed beam directions. Rotational IMRT is achieved by dynamically changing collimator aperture shapes as the gantry moves around the patient in one or more sweeps along an arc during radiation delivery. Intensity-modulated arc therapy ("IMAT"), a rotational IMRT delivery technique, was first proposed as an alternative to tomotherapy. In tomotherapy, a narrow multileaf collimator ("MLC") is used to control aperture shapes as the radiation source rotates about the patient. At the same time, the couch on which the patient rests is translated. In contrast, IMAT is performed with a conventional linear accelerator, and the large set of tungsten leaves of the MLC is used to change the "shape" of the aperture as the gantry rotates during delivery.

In IMAT, the treatment is delivered along arcs with a single sweep or multiple sweeps, each with a start and stop position, and the patient remains stationary during the delivery process. The MLC field shape changes continuously during gantry rotation between a collection of specified apertures. Typically, apertures are specified at a set of equally-spaced angles that may be referred to as an "angle grid." An estimate of the radiation delivered to the patient can then be made by summing the radiation delivered from the angle grid. Note that multiple overlapping arcs provide multiple apertures at each angle and, thereby, yield a modulated intensity distribution from each delivery angle. Thus, an approach to IMAT treatment planning that reflects procedures typically used in IMRT treatment planning is to compute a collection of idealized real-valued fluence matrices over the angle grid, and then approximate these matrices by weighted sums of binary matrices corresponding to the collection of apertures at each angle. These weights and apertures are typically chosen to minimize the approximation error subject to delivery constraints.

A key advantage of IMAT is that the delivery is achieved using a conventional linear accelerator and a conventional MLC. Therefore, IMAT treatments can be delivered using existing equipment in most radiation oncology departments. However, it should be noted that to deliver IMAT plans, the linear accelerator must be equipped with the capability for dynamic delivery. Elekta volumetric arc therapy ("VMAT") and Varian Medical Systems rapid arc VMAT are two commercially available IMAT systems that, generally, use only a single sweep through one arc for treatment delivery. In some instances, additional sweeps may be used to treat cases involving complex geometries.

Traditionally, IMRT treatment plans are generated with either a two-step process, or a direct aperture optimization ("DAO") process. In two-step processes, the matrices of beamlet (also called pencil beam) intensities for the set of specified beam directions are optimized. The resulting optimized intensity matrices or maps are then sent to a leaf-sequencer that determines, via the solution of segmentation problems, the set of deliverable MLC shapes and intensities that are combined to approximate each optimized intensity map. It is in this step where any delivery constraints of the treatment unit are enforced. The output of the two-step procedure is a set of MLC aperture shapes and their corresponding weights (known clinically as monitor units) that are referred to as a "segmentation." In contrast, DAO methods do not utilize optimized intensity maps, but instead generate sets of apertures that are appropriate for each angle and then seek to weight, and sometimes modify, these apertures in order to obtain a desirable dose distribution.

SUMMARY OF THE INVENTION

A system and method for producing an intensity modulated arc therapy ("IMAT") treatment plan are provided. A plurality of segmentations are generated for each delivery angle, from which the IMAT treatment plan is determined. Apertures within each segmentation are ordered by minimizing the total leaf movement between sets of aperture shapes corresponding to adjacent delivery angles. From these segmentations, a network model is used to select those segmentations to be used in the IMAT treatment plan. The selected segmentations may be modified to minimize total leaf movement relative to apertures in the selected segmentations while satisfying physical constraints, such as a maximum leaf movement or interdigitation constraint. Segmentation errors are then locally minimized using a network model and, for example, a row-non-convexity measure, which is used to determine the order in which the apertures will be selected for modification. For example, apertures may be modified one at a time using the aforementioned network model and in an order related to the row-non-convexity measure.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A system and method for designing a radiation treatment plan for an intensity-modulated arc therapy ("IMAT") system is provided. An efficient network-based approach is utilized to find an IMAT treatment plan with a small number of arcs and, hence, a small number of apertures per beam angle. The treatment plan is designed to well approximate desired intensity map fluences on a given angle grid. Such an approach requires a complex leaf-sequencing algorithm that takes into account constraints between the aperture shapes at consecutive angles resulting from mechanical limitations on leaf movement. This constraint is referred to as a maximum leaf movement limit, and is discussed below.

Figure 1:
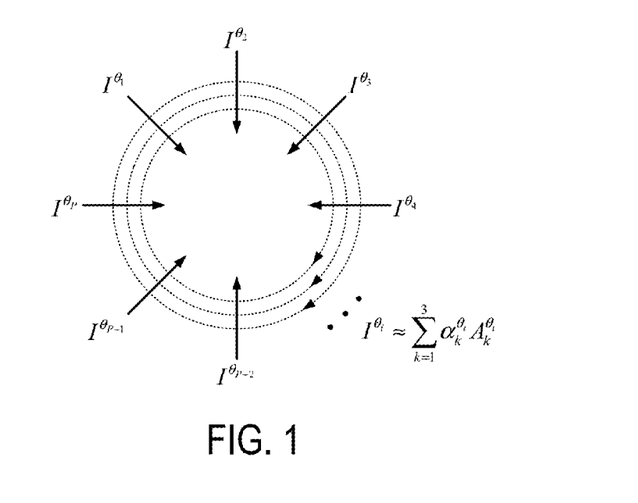
FIG. 1 is a graphic illustration of an example of a radiation treatment plan for intensity-modulated arc therapy ("IMAT"), in which three sweeps are used.

With reference to FIG. 1, an IMAT treatment plan is generally delivered along a set of K arcs by specifying apertures, A, and intensities, I, on an angle grid of control points. Such an angle grid contains P, usually equally-spaced, angles, $\theta_1, \ldots, \theta_P$, that span the arcs. The illustration in FIG. 1 includes a delivery through three arcs (K=3).

By way of example, a set of P intensity maps can be expressed as:

$$\{I^{\theta_1}, I^{\theta_2}, \ldots, I^{\theta_i}, \ldots, I^{\theta_P}\} \quad (1);$$

where $i=1, 2, \ldots, P$, and each intensity map, $I^{\theta_i}$, is an m×n non-negative real matrix that represents the beamlet fluences that would be delivered in total over the K sweeps at the control point, $\theta_i$. To approximate these ideal fluences, for each angle in the angle grid, a segmentation of K aperture shapes for a given intensity map, $I^{\theta_i}$, is generated. That is, the following set of intensity-aperture pairs is generated:

$$S^{\theta_i} := \{(\alpha_k^{\theta_i}, A_k^{\theta_i}) : k=1, \ldots, K\} \quad (2);$$

where $\alpha_k^{\theta_i}$ represents the beam-on-time, or intensity, through the aperture, $A_k^{\theta_i}$. By way of example, $\alpha_k^{\theta_i}$, is assumed to be non-negative. The intensity map, $I^{\theta_i}$, may be approximated via the sum:

$$I^{\theta_i} \approx \sum_{k \in [K]} \alpha_k^{\theta_i} A_k^{\theta_i}; \quad (3)$$

where [K] is the following set:

$$[K] = \{1, 2, \ldots, K\} \quad (4).$$

Figure 2:
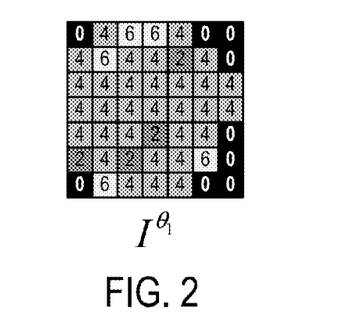
FIG. 2 is a pictorial representation of an example of an intensity map that forms a part of an IMAT treatment plan.
Figure 3:
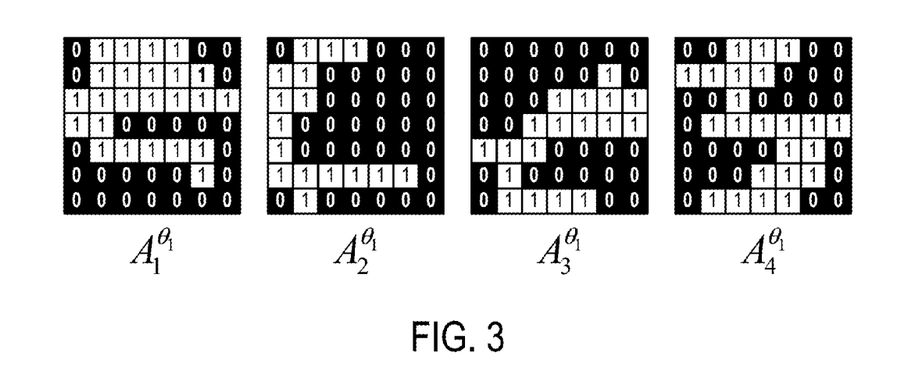
FIG. 3 is a pictorial representation of an example of aperture shapes that may be used to produce the intensity map of FIG. 2.

The aperture, $A_k^{\theta_i}$, may be represented by a binary matrix whose elements have a value of one if that beamlet is part of the shape. An exemplary intensity map is illustrated in FIG. 2, and the corresponding apertures whose weighted sum results in the intensity map are illustrated in FIG. 3.

Because the set of open beamlets in each row of the collimator is determined by the separation of a pair of opposing leaves of a multileaf collimator, any nonzero row of an achievable shape contains a single interval of ones. This property is called the single-interval constraint, which will be described in further detail below. Another common constraint that will be described below in further details, and that is advantageous when used for forming a deliverable aperture shape, is the interdigitation constraint, which does not allow opposing adjacent leaves to cross each other. The interdigitation constraint is not present in all multileaf collimators, but is present in several widely-used machines.

Unlike fixed gantry intensity-modulated radiation therapy, IMAT segmentations have to satisfy a maximum leaf movement constraint that forces the segmentations corresponding to two adjacent angles in an arc to have pairs of fairly closely overlapping apertures. This constraint arises from physical constraints on the speed at which a leaf can change its position and, thus, the overall aperture shape of the multileaf collimator. Thus, in IMAT, it is desirable to produce a segmentation with K apertures shapes that approximates the intensity matrices, $I^{\theta_i}$, and that also adheres to leaf movement constraints between aperture shapes on adjacent angles.

Such highly constrained segmentations often result in large approximation errors; thus, generating segmentations that yield close to the minimum possible error is a very challenging problem. In practice, relatively few sweeps (K is typically between 1 and 6) will be performed, so it may be advantageous to select segmentations with a relatively small number of aperture shapes.

By way of example, and for purposes of designing an IMAT radiation treatment plan, at each given angle, $\theta_i$, a selected number, Q, of possible segmentations, $S_j^{\theta_i}$, is available to choose from as indicated by:

$$S_j^{\theta_i}, j \in [Q] \quad (5).$$

It is therefore desirable to determine which segmentations, $S_j^{\theta_i}$, to use at a given angle, $\theta_i$, from among the Q choices. Note that, having chosen this segmentation, a collection of K aperture shapes at each angle, $\theta_i$, exists. Each of these aperture shapes is then assigned to a particular sweep.

As will be described below in detail, the general approach of the present invention is to solve the sweep assignment problem using a framework that uses a network approach that, given two successive angles and their corresponding segmentations, determines which aperture shape should be assigned to which sweep. Because this approach is very inexpensive computationally, it is applied at all angles, $\theta_i$, and for all segmentations, $S_j^{\theta_i}$. Using the results from this step as input data, another network model is used to determine the optimal combination of segmentations over the set of angles. A feasibility step is employed next in order to modify apertures as needed to enforce maximum leaf motion constraints and any additional mechanical constraints that may be present. Finally, a local improvement procedure is applied to optimize over arbitrary feasible apertures, rather than considering only fixed apertures from the pre-determined segmentations.

Figure 4:
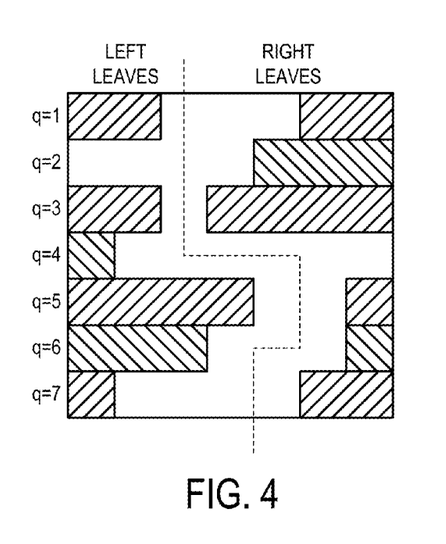
FIG. 4 is a graphic illustration of an example of a multileaf collimator ("MLC") having an aperture shape representative of the example aperture $A_4^{\theta_1}$ illustrated in FIG. 3.

As noted above, the general segmentation problem is to determine deliverable aperture shape matrices, $\{A_k^{\theta_i}: k=1, \ldots, K\}$, along with beam intensities, $\{\alpha_k^{\theta_i}: k=1, \ldots, K\}$, that approximate a given m×n nonnegative intensity map, $I^{\theta_i}$. Deliverable can mean different things for different treatment systems. The two common physical constraints mentioned above, the single-interval constraint and interdigitation constraint, are now presented in more particular detail. With reference to FIG. 4, an exemplary multileaf collimator having seven rows of leaves is illustrated. For an aperture shape, $A_k^{\theta_i}$, the binary variables $l_k[q,t]$ and $r_k[q,t]$, with $q \in [m]$ and $t \in [n]$, may be defined as being set to values of one to indicate beamlets [q,t] covered by the left leaf in the $q^{th}$ row of a multileaf collimator, and the right leaf in the $q^{th}$ row of a multileaf collimator, respectively. For the $q^{th}$ row of the aperture shape $A_k^{\theta_i}$, the single-interval constraint can be formulated as:

$$\sum_{t \in [n]} l_k[q, t] + \sum_{t \in [n]} r_k[q, t] \le n, \quad (6)$$

$$l_k[q, t] \ge l_k[q, t+1],$$

$$r_k[q, t] \le r_k[q, t+1];$$

where for the constraints, $l_k[q,t] \ge l_k[q,t+1]$ and $r_k[q,t] \le r_k[q,t+1]$, $t \in [n-1]$. For the $q^{th}$ and $(q+1)^{th}$ rows of the aperture shape $A_k^{\theta_i}$, the interdigitation constraint can be formulated as:

$$\sum_{t \in [n]} l_k[q, t] + \sum_{t \in [n]} r_k[q+1, t] \le n, \quad (7)$$

$$\sum_{t \in [n]} l_k[q+1, t] + \sum_{t \in [n]} r_k[q, t] \le n;$$

subject also to the constraints $l_k[q,t] \ge l_k[q,t+1]$ and $r_k[q,t] \le r_k[q,t+1]$, for $t \in [n-1]$. For a given m×n intensity map, $I^{\theta_i}$, and a nonnegative real number $\epsilon < 1$, a projection map, $P_\epsilon(I^{\theta_i})$, can be defined as an m×n binary matrix where the $(i, j)^{th}$ entry of $P_\epsilon(I^{\theta_i})$ is equal to one if and only if the $(i, j)^{th}$ entry of the intensity map, $a_{ij}$, is greater than $\epsilon \cdot \max_{i,j}\{a_{ij}\}$. The projection, $P_\epsilon(I^{\theta_i})$, is called row-convex if it satisfies the single-interval constraint. The intensity map, $I^{\theta_i}$, is called row-convex if $P_\epsilon(I^{\theta_i})$ is row-convex for all $\epsilon < 0$; otherwise, it is called row-non-convex.

Thus, an aperture shape matrix, $A_k^{\theta_i}$, that satisfies the single-interval constraint is an example of a row-convex intensity map, $I^{\theta_i}$. It can be intuitively seen that row-non-convexity of $I^{\theta_i}$ results in higher segmentation errors in feasible IMAT solutions because the solution components, which are the aperture shapes, themselves must be row-convex. A row-non-convexity measure, $\rho(I^{\theta_i})$, that may be used to identify the amount of row-non-convexity of an intensity map is now defined. The prior knowledge of arc-segments that contain row-non-convex intensity maps helps focus computational effort on difficult-to-approximate intensity maps.

In order to define the row-non-convexity measure, $\rho(I^{\theta_i})$, the relative error measure that is used for a given segmentation, $S_j^{\theta_i} = \{(\alpha_k^{\theta_i}, A_k^{\theta_i}) : k \in [K]\}$, is first described as:

$$err(I^{\theta_i}, S_j^{\theta_i}) = \frac{\left\| I^{\theta_i} - \sum_{k \in [K]} \alpha_k^{\theta_i} A_k^{\theta_i} \right\|_{1^*}}{\| I^{\theta_i} \|_{1^*}}; \quad (8)$$

where, $$\|x\|_{1^*} = \left( \sum_{i=1} |x_i| \right); \quad (9)$$

denotes the 1*-norm of a matrix that is viewed as a single vector, x, that contains all of the components of the matrix.

For a given intensity matrix, $I^{\theta_i}$, and a positive integer, K, it is desirable to find a segmentation, $S_j^{\theta_i}$, that minimizes the relative error over the set of apertures that satisfy the machine specific constraints. This minimization can be formulated as follows:

$$\min_{S_j^{\theta_i}} \{err(I^{\theta_i}, S_j^{\theta_i})\} \text{ such that } S_j^{\theta_i} = \{(\alpha_k^{\theta_i}, A_k^{\theta_i}) : k \in [K]\}; \quad (10)$$

where $A_k^{\theta_i} \in FA$ and $\alpha_k^{\theta_i} \ge 0$. Here, the term FA represents the set of binary matrices that satisfy the machine specific constraints. Note that the variables of this problem are the $\alpha_k^{\theta_i}$ and $A_k^{\theta_i}$. This problem is called unconstrained if FA is taken as the set of all m×n binary matrices, B.

Let:

$$ul_K(e) = \min \left\{ \frac{\left\| I^{\theta_i} - \sum_{k \in [K]} \alpha_k^{\theta_i} A_k^{\theta_i} \right\|_{1^*}}{\| I^{\theta_i} \|_{1^*}} : A_k^{\theta_i} \in B \right\}; \quad (11)$$

be the unconstrained solution, and let:

$$l_K(e) = \min \left\{ \frac{\left\| I^{\theta_i} - \sum_{k \in [K]} \alpha_k^{\theta_i} A_k^{\theta_i} \right\|_{1^*}}{\| I^{\theta_i} \|_{1^*}} : A_k^{\theta_i} \in FA \right\}; \quad (12)$$

be the constrained solution.

Furthermore, let F' be all the binary matrices that satisfy the single-interval constraint, and let:

$$l'_K(e) = \min \left\{ \frac{\left\| I^{\theta_i} - \sum_{k \in [K]} \alpha_k^{\theta_i} A_k^{\theta_i} \right\|_{1^*}}{\| I^{\theta_i} \|_{1^*}} : A_k^{\theta_i} \in F' \right\}; \quad (13)$$

be the single-interval constrained solution.

The row-non-convexity measure, $\rho(I^{\theta_i})$, of the intensity map, $I^{\theta_i}$, can then be defined by comparing the single-sweep, single-interval constrained solution to the unconstrained solution as follows:

$$\rho(I^{\theta_i}) = l'_1(e) - ul_1(e) \quad (14)$$

$$= \frac{\min_{A_k^{\theta_i} \in F', \alpha_k^{\theta_i}} \| I^{\theta_i} - \alpha_k'^{\theta_i} A_k'^{\theta_i} \|_{1^*} - \min_{A_k^{\theta_i} \in B, \alpha_k^{\theta_i}} \| I^{\theta_i} - \alpha_k^{\theta_i} A_k^{\theta_i} \|_{1^*}}{\| I^{\theta_i} \|_{1^*}}.$$

Because $F' \subset B$, it can be shown that $0 \le \rho(I^{\theta_i}) \le 1$.

The provided systems and methods for designing an optimal IMAT radiation treatment plan utilize a unique framework that operates on a plurality of segmentations, $S_j^{\theta_i}$, that may be provided to the framework from any number of different algorithms for generating such segmentations. Generally, the framework includes the use of three network models. The first network model addresses the issue of ordering the apertures for segmentations in terms of sweep assignment. The second network model is used to identify the segmentation, $S_j^{\theta_i}$, which is a collection of K intensities and apertures, to use at each angle, $\theta_i$. The third network model locally optimizes the aperture shapes to reduce segmentation errors of a given feasible IMAT solution. A description of each of these three network models is now given in detail.

The first network model is concerned with the problem of morphing one collection of aperture shapes into another as the collimator is moved along the sweeps, and can therefore be referred to as an aperture ordering network model. To do this, the total leaf movement required to morph one aperture shape, A, into another aperture shape, A', is considered. By way of example, let l(j) be the amount of the $j^{th}$ left leaf movement between aperture shape A and A', and let r(j) be the amount of the $j^{th}$ right leaf movement between the two aperture shapes. Then the total leaf movement, TLM, between the two aperture shapes may be given by:

$$TLM(A, A') = \sum_{j \in [m]} l(j) + r(j). \tag{15}$$

Provided that open beamlets overlap, the total leaf movement is the sum of the absolute differences between the binary matrices for the aperture shapes, A and A'. Because this problem does not depend on intensities, $\alpha_k^{\theta_i}$, but simply on the apertures, the dependence of the segmentations on the intensities can be removed for ease of presentation.

Given two angles $\theta$ and $\phi$ with given segmentations:

$$S^\theta = \{A_k^\theta : k \in [K]\} \tag{16}$$

and $$S^\phi = \{A_k^\phi : k \in [K]\} \tag{17}$$

each aperture shape $A_k^\phi$ is uniquely assigned to an aperture shape $A_k^\theta$ in order to minimize the total overall leaf movement between all pairs of aperture shapes. This ordering problem may be solved as the following assignment problem:

$$\min_x \sum_{k \in [K]} \sum_{k' \in [K]} x_{kk'} TLM(A_k^\theta, A_{k'}^\phi); \tag{18}$$

subject to:

$$\sum_{k \in [K]} x_{kk'} = 1 \text{ for } k' \in [K]; \tag{19}$$

$$\sum_{k' \in [K]} x_{kk'} = 1 \text{ for } k \in [K]; \tag{20}$$

and $$x_{kk'} \in \{0, 1\}. \tag{21}$$

Given the solution of the assignment problem, it can be shown that if $x_{kk'}=1$, then for a particular sweep, if aperture k is used at angle $\theta$, then aperture k' should be used at angle $\phi$. In the discussion below, an aperture k' determined in this manner is referred to as the optimal successor of aperture k with respect to the segmentation pair $S^\theta$, $S^\phi$.

Typically, the angle $\phi$ is the next angle in a given sweep. The TLM minimum value from the above assignment problem to morph from $S_j^{\theta_i}$ to $S_j^{\theta_{i+1}}$ is denoted by $c_{jj}^{\theta_i}$), and will be used in the objective function of the second network model, which determines which segmentation to use at each angle.

In practice, minimizing total leaf movement between two consecutive aperture shapes is a surrogate for the physical constraint on the maximum leaf movement between two consecutive aperture shapes. Formally, given two aperture shapes $A_k$ and $A_{k'}$, this is defined as:

$$MLM(A_k, A_{k'}) = \max\{maxmove(i) | i \in [m]\} \tag{22}$$

where:

$$maxmove(i) = \max\{l(i), r(i)\} \tag{23}$$

In experiments using MLM as an objective measure in the aperture ordering problem instead of TLM, the assignments produced did not generally satisfy the MLM constraint and did not generally differentiate between solutions with the same MLM, but radically different TLM values. Thus, it is contemplated that this alternative objective is less accurate. A composite objective of MLM+μ·TLM for appropriate values of μ may, however, be an advantageous choice of objective for the aperture ordering problem.

Figure 5:
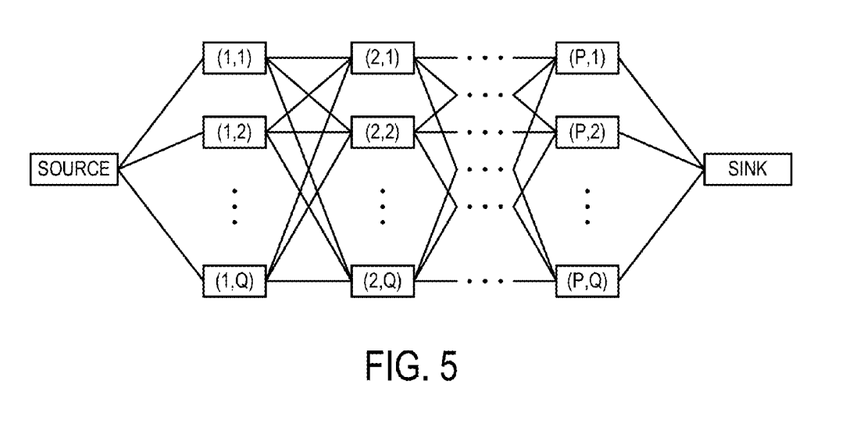
FIG. 5 is a pictorial representation of an example of a network model for determining segmentations to be included in an IMAT treatment plan.

For the second network model, which is concerned with the selection of segmentations and can therefore be referred to as a segmentation selection network model, it is assumed that at each angle, $\theta_i$, a collection of Q segmentations, $S_j^{\theta_i}$, with $j \in [Q]$, exists. In practice, it is supposed that at each angle, $\theta_i$, Q different segmentation algorithms can be applied to generate these segmentations. In general, the second network model chooses the segmentation, $S_j^{\theta_i}$, to be used at each angle. The following information is typically used as an input to the second network model. First, the TLM minimum values, $c_{jj'}^{\theta_i}$, for each angle, $\theta_i$, and each angle-adjacent pair of segmentations, $S_{jj'}^{\theta_i}$, are input. Additionally, the segmentation error at each angle, $\theta_i$, for each segmentation, $S_j^{\theta_i}$, can be supplied to the second network model. This segmentation error may be calculated according to:

$$e_{ij} = err(I^{\theta_i}, S_j^{\theta_i}) \tag{24}$$

where $I^{\theta_i}$, represents the intensity matrix at the angle, $\theta_i$.

The second network model is constructed with nodes (i, j) corresponding to angles $\theta_i$ and segmentations $S_j^{\theta_i}$ for $i \in [P]$ and $j \in [Q]$. An exemplary network for the second network model is illustrated in FIG. 5.

A cost for each arc is assigned as follows. The cost of the arc between the node (i, j) and the node (i+1, j') is equal to:

$$\frac{1}{2}(e_{ij} + e_{i+1,j'}) + \gamma c_{jj'}^{\theta_i}; \tag{25}$$

where γ is a nonnegative constant. Additionally, the cost of the arc between source and node (1, j) is:

$$\frac{1}{2}e_{1j}; \tag{26}$$

and the cost of the arc between node (P, j) and sink is $$\frac{1}{2}e_{Pj}. \tag{27}$$

To illustrate this approach, consider a simple case in which there are three angles (P=3) and only two segmentations at each angle (Q=2). In this example, there are eight feasible solutions to this problem, corresponding to the eight paths between the supply and demand nodes. Suppose that the optimal path involves the nodes (1,2), (2,1), and (3,2). This means segmentation $S_2^{\theta_1}$ will be used at angle $\theta_1$, segmentation $S_1^{\theta_2}$ will be used at angle $\theta_2$, and segmentation $S_2^{\theta_3}$ will be used at angle $\theta_3$. Note that the number of sweeps, K, does not appear in this data. However, the optimal path dictates the sweep composition. Because the optimal path goes from (1,2) to (2,1), the calculation of the cost, $c_{21}^{\theta_1}$, assigns a successor aperture shape to each aperture in $S_2^{\theta_1}$. Thus, in sweep k=1, the first aperture of segmentation $S_1^{\theta_1}$ is used at angle $\theta_1$; its optimal successor aperture, k', from segmentation $S_1^{\theta_2}$, as determined by the assignment solution from the first network model, is used at angle $\theta_2$; and the appropriate optimal successor of aperture k' from segmentation $S_2^{\theta_3}$ is used at angle $\theta_3$. Analogous observations apply to sweep k=2. The second sweep starts with the second aperture of segmentation $S_2^{\theta_1}$, and then uses its optimal successor from segmentation $S_1^{\theta_2}$ at angle $\theta_2$, and so on.

Note that the solutions produced by solving problems associated with this network may not be feasible with respect to maximum leaf movement constraints. As will be described below, an optimization procedure for obtaining such a feasible solution is achievable by modifying the solution of a problem associated with the aforementioned network model. This feasible solution may be input to the third network model, described below, which locally optimizes segmentation error.

In the third network model, which is concerned with optimizing segmentation error and can therefore be referred to as a segmentation error network model, a feasible IMAT treatment plan with K sweeps, and for which the maximum leaf movement is at most D between consecutive angles, is used as input. For example, the aperture ordering and segmentations identified using the first and second network models can be modified to form a feasible IMAT treatment plan for inputting into the third network model.

The third network model seeks to modify the aperture that is found on the $k^{th}$ sweep at angle $\theta_i$ within the segmentation $S_j^{\theta_i}$ to reduce the error measure, $err(I^{\theta_i}, S_j^{\theta_i})$. The constraints relevant to such an aperture shape are the machine specific constraints, A∈FA, and the maximum leaf movement constraints between the current aperture shape and the previous and next aperture shapes in the sweep.

More particularly, the third network model is used to find the aperture, A, that solves the following error minimization problem:

$$\min_A \{err(I^{\theta_i}, S_j^{\theta_i})\}; \quad (28)$$

subject to the following:

$$S_j^{\theta_i} = \{(\alpha_q, A_q): \alpha_q = \alpha_q^{\theta_i}, A_q = A_q^{\theta_i}, q \neq k, \alpha_k = \alpha_k^{\theta_i}, A_k = A\} \quad (29);$$

where:

$$A \in FA \quad (30);$$

$$MLM(A_k^{\theta_{i-1}}, A) \leq D \quad (31);$$

and $$MLM(A, A_k^{\theta_{i+1}}) \leq D \quad (32).$$

The network is built as follows. For the aperture shape, $A_k^{\theta_i}$, let $L_{i,k}(r)$ denote the end of the left leaf for a row aperture opening, r; and $R_{i,k}(r)$ denote the end of the right leaf for a row aperture opening, r. For notational simplicity, the construction of the network is illustrated for the special case in which the aperture at the second angle has been selected for optimization, so that the apertures at the adjacent first and third angles are fixed and determine the maximum leaf movement constraints for the second angle. The set of nodes is defined as a supply node (source), a demand node (sink), and:

$$\left\{\begin{array}{c}(r, t_1, t_2): \max(L_{1,k}(r), L_{3,k}(r)) - \\ D \leq t_1 \leq \min(L_{1,k}(r), L_{3,k}(r)) + D \\ \max(L_{1,k}(r), R_{3,k}(r)) - D \leq t_2 \leq \min(R_{1,k}(r), L_{3,k}(r)) + D \\ 0 \leq t_1 \leq t_2 \leq n+1\end{array}\right\}; \quad (33)$$

Note that for each r between 1, . . . , m, there exists at least one node due to the feasibility of the starting IMAT treatment plan solution, and the node $(r, t_1, t_2)$ represents an $r^{th}$ row aperture opening with the set of beamlets $\{[r,t]:t \leq t_1\}$ covered by the $r^{th}$ left leaf, and the set of beamlets $\{[r,t]:t \geq t_2\}$ covered by the $r^{th}$ right leaf. There is an arc between nodes $(r, t_1, t_2)$ and $(r+1, t_3, t_4)$ if the combination of the corresponding aperture openings for those two nodes forms a feasible aperture for the machine specific constraints, such as for the interdigitation constraint, where $t_3 < t_2$ and $t_1 < t_4$. There are arcs defined between the supply node and all the nodes in the first row, and all the nodes in the $m^{th}$ row and the demand node.

A cost for each defined arc is assigned as follows. The cost of the arc between the nodes $(r, t_1, t_2)$ and $(r+1, t_3, t_4)$ is equal to:

$$\frac{1}{2}(e_{r,t_1,t_2} + e_{r+1,t_3,t_4}); \quad (34)$$

where $e_{r,t_a,t_b}$ is an error parameter defined as the absolute change in the segmentation error of $I^{\theta_i}$, when the aperture opening of the $r^{th}$ row of $A_k^{\theta_i}$ is replaced by the opening corresponding to the node $(r, t_a, t_b)$. Thus, the cost of the arc between source and $(1, t_a, t_b)$ is equal to:

$$\frac{1}{2}e_{1,t_a,t_b}; \quad (35)$$

and the cost of the arc between $(1, t_a, t_b)$ and sink is equal to:

$$\frac{1}{2}e_{m,t_a,t_b}. \quad (36)$$

The supply at source is +1 and the demand at sink is −1, and the problem can be viewed as a shortest path problem that minimizes:

$$err(I^{\theta_i}, S) = \frac{\left\|I^{\theta_i} - \alpha_k^{\theta_i}A - \sum_{q \in [K], q \neq k}\alpha_q^{\theta_i}A_q^{\theta_i}\right\|_{1*}}{\|I^{\theta_i}\|_{1*}}; \quad (37)$$

for IMAT feasible apertures, A.

Figure 6:
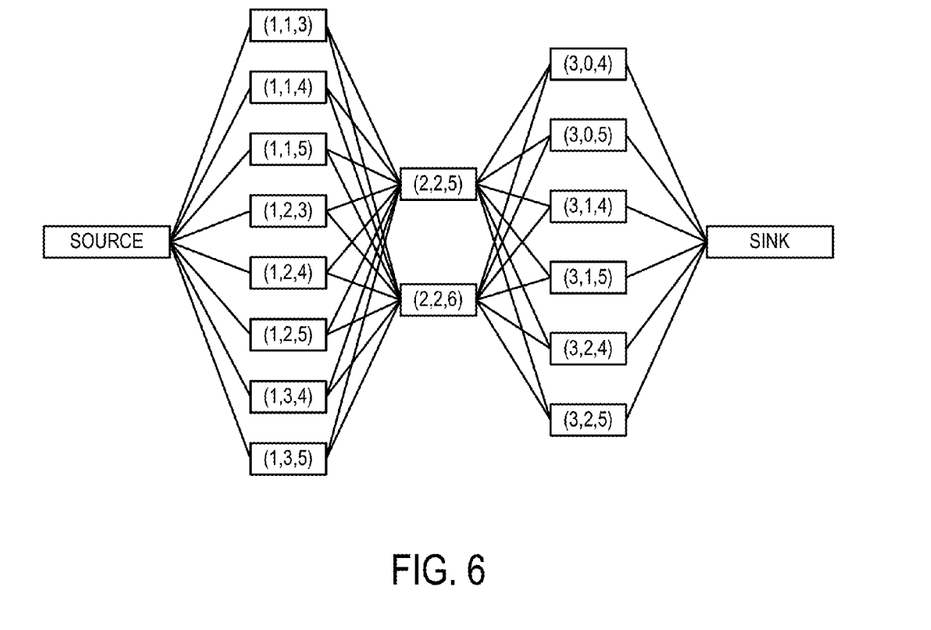
FIG. 6 is a pictorial representation of an example of a network model for minimizing segmentation errors in an IMAT treatment plan.

As a simple example, consider an IMAT case where D=2, k=1, and $A_1^{\theta_1}$ and $A_1^{\theta_3}$ are 3×6 aperture shapes as follows:

$$A_1^{\theta_1} = \begin{pmatrix} 010000 \\ 111000 \\ 110000 \end{pmatrix}; \quad (38)$$

-continued $$A_1^{\theta_3} = \begin{pmatrix} 000100 \\ 000011 \\ 011110 \end{pmatrix}. \quad (39)$$

Table 1 shows the parameters to build the aforementioned network model to optimize $A_1^{\theta_2}$ with respect to the segmentation error and FIG. 6 shows the corresponding network model.

TABLE 1

| r | $L_{1,1}(r)$ | $R_{1,1}(r)$ | $L_{3,1}(r)$ | $R_{3,1}(r)$ | $t_1$ | $t_2$ |
|---|---|---|---|---|---|---|
| 1 | 1 | 3 | 3 | 5 | 1, 2, 3 | 3, 4, 5 |
| 2 | 0 | 4 | 4 | 7 | 2 | 5, 6 |
| 3 | 0 | 3 | 1 | 6 | 0, 1, 2 | 4, 5 |

Figure 7:
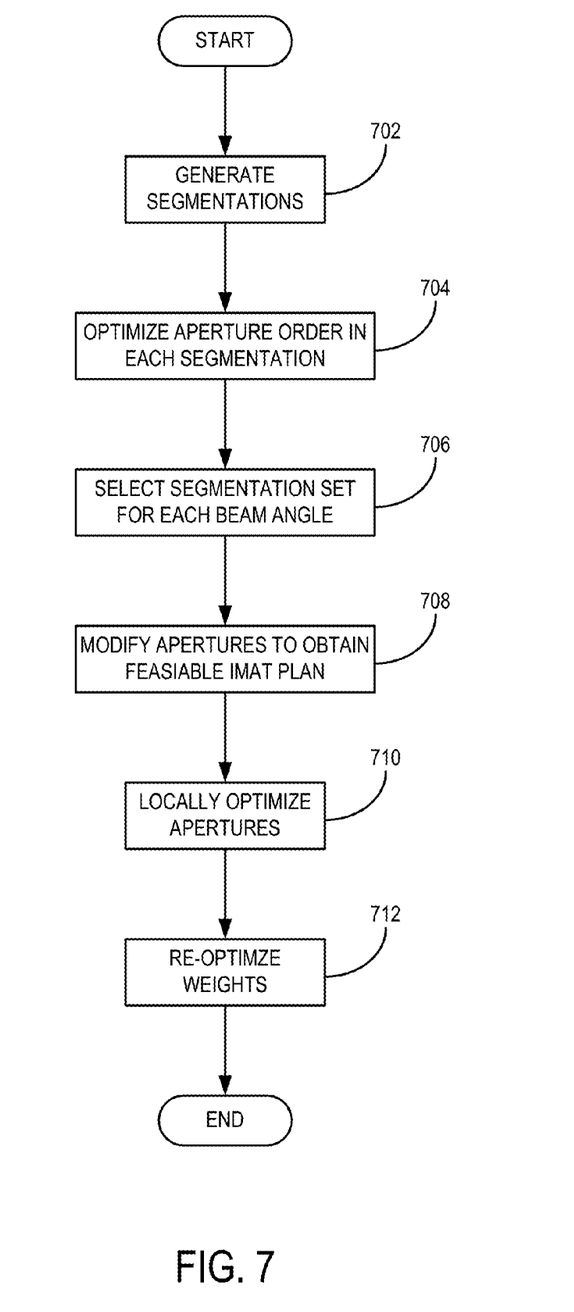
FIG. 7 is a flowchart setting forth the steps of an example of a method for designing an IMAT treatment plan.

Referring particularly now to FIG. 7, a method for designing a radiation treatment plan for an intensity modulated arc therapy ("IMAT") system in accordance with some embodiments of the invention is illustrated. The method generally begins with the generation of a set of segmentations from which the treatment plan will be designed, as indicated at step 702. Known methods for generating such segmentations exist and any suitable method can be employed. For example, segmentation methods may include modified difference matrix metaheuristic algorithms, greedy error reduction segmentation algorithms, left-right segmentation algorithms, near-optimal segmentation algorithms, and the like. It is an advantage of the present invention that more than one segmentation algorithm can be employed and that segmentations generated from different segmentation algorithms can be combined in the resulting treatment plan. By way of example, a number, Q, of segmentations, each having a number, K, of aperture shapes for each angle, $\theta_i$, is generated. It is advantageous to use segmentations that produce relatively small errors and that are not substantially similar to each other.

After the desired number of segmentations has been generated, an approximate solution to the IMAT aperture ordering optimization problem is found by minimizing total leaf movement between segmentation pairs at adjacent angles, as indicated at step 704. Then, as indicated at step 706, a selection, $j(\theta_i)$, is made of one segmentation $S_{j(\theta_i)}^{\theta_i}$ of the intensity map $I^{\theta_i}$ for each angle, $\theta_i$, with $i \in [P]$. These selections are referred to as:

$$\overline{S}^{\theta_i} = S_{j(\theta_i)}^{\theta_i} \quad (40).$$

By way of example, each selection is identified by building a segmentation selection network model, such as the second network model discussed above in detail, using the ordering of the segments at each angle determined by the solutions of the assignment problems solved using the aperture ordering network model, such as the first network model discussed above in detail. The shortest path of the segmentation selection network model is then solved via linear programming or any other suitable optimization method. By way of example, these problems may be solved in less than one second for $Q \leq 10$. Then, the segmentations, $\overline{S}^{\theta_i}$, of $I^{\theta_i}$ that lie on the resulting flow path are then selected as the identified segmentations.

Next, a feasible IMAT treatment plan is generated by modifying apertures as needed to minimize the total leaf movement relative to the apertures using physical constraints, as indicated at step 708. The segmentations identified in step 706 are used as the input for this step. In this step, a feasible IMAT treatment plan solution that satisfies, for example, the maximum leaf movement constraint and the interdigitation constraint is developed. For example, minimum changes are made to the set of feasible shapes $\overline{S}$ that are produced in step 706 to obtain a set of shapes $\hat{S}$. Thus, the segmentations selected by the second network model, $\overline{S}^{\theta_i}$ of $I^{\theta_i}$, for $i \in [P]$, are used to produce a set of segmentations, for $\hat{S}^{\theta_i}$ for $I^{\theta_i}$, $i \in [P]$, where:

$$\hat{S}^{\theta_i} = \{(\alpha_k^{\theta_i}, \hat{A}_k^{\theta_i}) : k \in [K]\} \quad (41);$$

satisfies the maximum leaf movement constraint, MLM $(\hat{A}_k^{\theta_i}, \overline{A}_k^{\theta_i}) \leq D$, and interdigitation constraint. By way of example, the segmentations $\hat{S}^{\theta_i}$ may be determined by solving the following problem:

$$\min \left\{ \sum_{i \in [P]} \sum_{k \in [K]} TLM(\hat{A}_k^{\theta_i}, \overline{A}_k^{\theta_i}) \right\}; \quad (42)$$

subject to the maximum leaf movement constraint:

$$MLM(\hat{A}_k^{\theta_i}, \hat{A}_k^{\theta_{i+1}}) \leq D \quad (43);$$

for $i \in [P-1]$ and $k \in [K]$, and also subject to interdigitation constraints for the given nonnegative integer, D. It is noted that this is a mixed-integer programming problem and, therefore, does not directly take into account segmentation errors; however, these segmentation errors are subsequently addressed, as indicated at step 710.

As noted, segmentation errors that may be present in the set of segmentations, $\hat{S}_j^{\theta_i}$, generated in step 708 are minimized in step 710. By way of example, a locally optimal IMAT treatment plan solution that minimizes segmentation errors may be found by modifying aperture shapes in the set of segmentations one at a time, with adjacent aperture shapes being fixed. Thus, the segmentations, $\hat{S}^{\theta_i}$ for $I^{\theta_i}$, $i \in [P]$, that are produced in step 708 may be used to produce segmentations, $\tilde{S}^{\theta_i}$ for $I^{\theta_i}$, $i \in [P]$, in which segmentations errors are substantially reduced. Generally, the third network model discussed above may be used to minimize the segmentation errors and to generate the aperture shapes $\tilde{A}_k^{\theta_i}$ in the segmentations $\tilde{S}_j^{\theta_i}$.

First, a sweep, k, is selected and the third network model, such as the segmentation error network model discussed above in detail, is applied to each angle in the sweep in descending order of the row-non-convexity measures, $\rho(I^{\theta_i})$. In this manner, the more difficult angles can be identified and processed accordingly. The aperture shape, $\hat{A}_k^{\theta_i}$, is then replaced with the aperture shape, $\tilde{A}_k^{\theta_i}$ given by the solution of the third network model to iteratively generate the segmentations, $\tilde{S}^{\theta_i}$. This process is repeated for each sweep. If there are no improvements in segmentation errors, which are given by:

$$err(I^{\theta_i}, \tilde{S}^{\theta_i}) \quad (44);$$

then the algorithm stops. Otherwise, the third network model is applied using the angles from left to right; that is, $i \in [P]$. Left-to-right iterations are repeated until there are no improvements in segmentation errors. Finally, the weights $\alpha_k^{\theta_i}$, $k \in [K]$ are optimized to get the minimum segmentation error for each angle, $\theta_i$, as indicated at step 712.

It is noted that smaller-than-needed values for leaf movement limit, D, can be used in step 708 while then relaxing this parameter back to its true value in step 710. This approach initially forces the apertures closer together and, thus, allows more flexibility for adjusting the "in-between" apertures in step 710.

Figure 8:
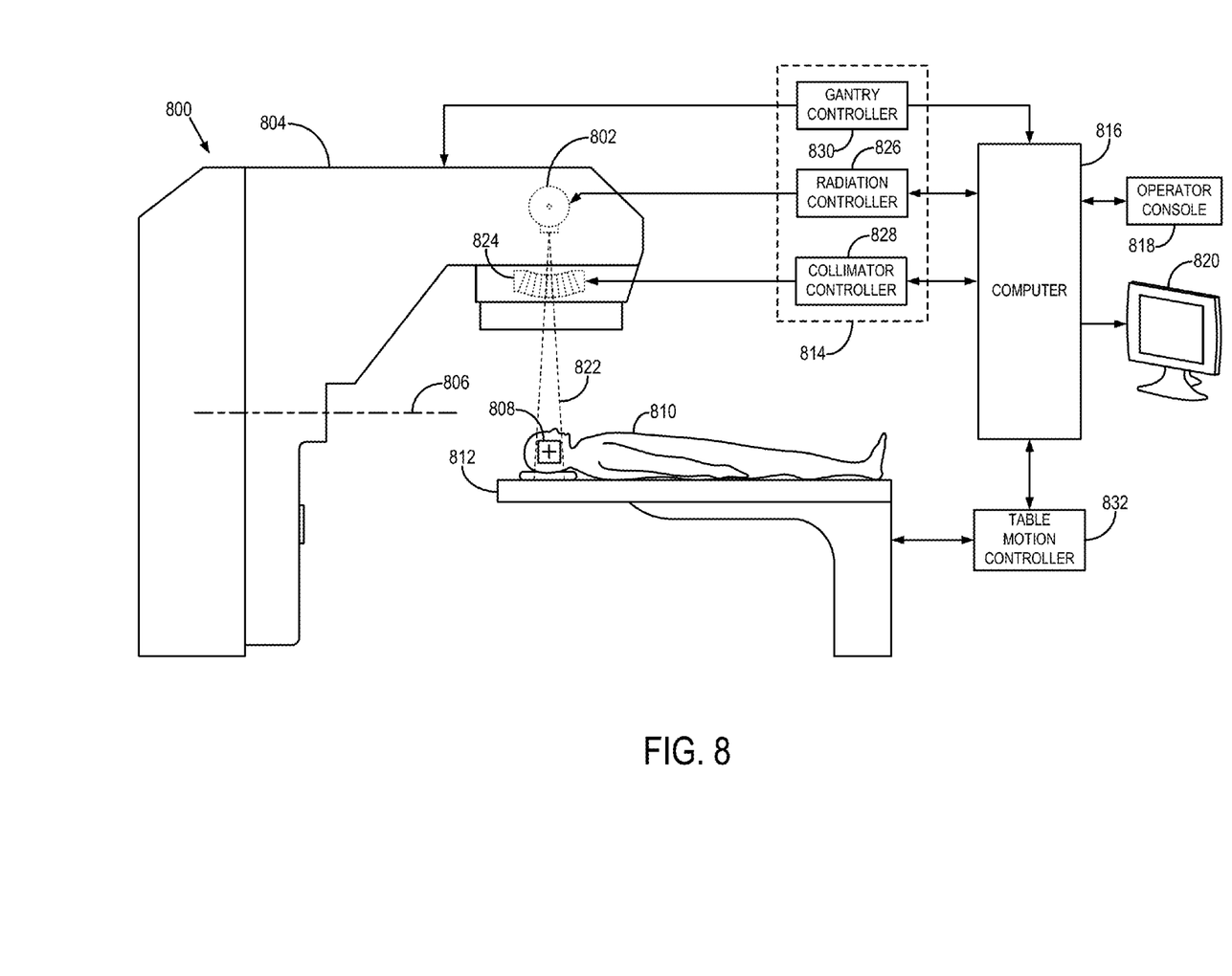
FIG. 8 is a block diagram of an example of an IMAT system.

Referring to FIG. 8, an example of an intensity-modulated arc therapy ("IMAT") system 800 that may be used when practicing the present invention includes a radiation source 802, such as an x-ray source, that is housed at an end of a rotatable gantry 804 that rotates about a rotation axis 806. The rotatable gantry 804 allows the radiation source 802 to be aligned in a desired manner with respect to a target volume 808 in a subject 810 positioned on a patient table 812. A control mechanism 814 controls the rotation of the gantry 804 and the delivery of radiation from the radiation source 802 to the target volume 808. The IMAT system 800 includes a computer 816 that receives commands and scanning parameters from an operator via a console 818, or from a memory or other suitable storage medium. An associated display 820 allows the operator to observe data from the computer 816, including images of the subject 810 that may be used to review or modify the treatment plan, and to position the subject 810 by way of appropriately adjusting the position of the patient table 812. The operator supplied commands and parameters may also be used by the computer 816 to provide control signals and information to the control mechanism 814.

The radiation source 802 produces a radiation beam 822, or "field," that is modulated by a collimator 824. The collimator 824 may include a multileaf collimator that is composed of a plurality of independently adjustable collimator leaves. In such a configuration, each leaf in the collimator 824 is composed of an appropriate material that inhibits the transmission of radiation, such as a dense radioopaque material, and may include lead, tungsten, cerium, tantalum, or related alloys.

The radiation source 802 is mounted on a rotatable gantry 804 that rotates about a rotation axis 806 so that the radiation beam 822 may irradiate the target volume 808 in the subject 810 from a variety of gantry angles, $\theta_i$. The radiation source 802 is controlled by a radiation controller 826 that forms a part of the control mechanism 814, and which provides power and timing signals to the radiation source 802.

A collimator controller 828, which forms a part of the control mechanism 814, controls the movement of each of the collimator leaves in and out of its corresponding sleeve. The collimator controller 828 moves the collimator leaves rapidly between their open and closed states to adjust the aperture shape of the collimator 824 and, therefore, the shape and fluence of the radiation beam 822. The collimator controller 828 receives instructions from the computer 816 to allow program control of the collimator 824.

A gantry controller 830, which forms a part of the control mechanism 814, provides the signals necessary to rotate the gantry 804 and, hence, to change the position of the radiation source 802 and the gantry angle, $\theta_i$, of the radiation beam 822 for the radiation therapy. The gantry controller 830 connects with the computer 816 so that the gantry 804 may be rotated under computer control, and also to provide the computer 816 with a signals indicating the gantry angle, $\theta_i$, to assist in that control. The position of the patient table 812 may also be adjusted to change the position of the target volume 808 with respect to the radiation source 802 by way of a table motion controller 832, which is in communication with the computer 816.

During operation of the IMAT system 800, the collimator controller 828 receives, from the computer 816, segmentation information indicating the aperture shape to be used for each gantry angle, $\theta_i$, during each sweep of the radiation source 802. The segmentations describe the intensity of the radiation beam 822 that is desired for each gantry angle, $\theta_i$.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a radiation therapy plan for intensity modulated arc therapy, in which a radiation source delivers radiation to a target volume in a subject while the radiation source traverses a plurality of delivery angles in at least one arc, the method comprising the steps of:
    a) generating a plurality of segmentations, each segmentation defining an intensity of radiation to be delivered from the radiation source to the target volume in the subject at one of the plurality of delivery angles of the radiation source;
    b) ordering apertures within each of the plurality of segmentations generated in step a) by minimizing total leaf movement between segmentations corresponding to adjacent delivery angles, and thereby calculating corresponding minimum total leaf movement values between such segmentations;
    c) selecting from the plurality of segmentations, a segmentation to be used at each of the plurality of delivery angles of the radiation source using the minimum total leaf movement values calculated in step b) and a network model having nodes that each correspond to both the plurality of delivery angles and the plurality of segmentations;
    d) generating apertures from the segmentations selected in step c) by minimizing total leaf movement relative to the segmentations selected in step c) subject to a maximum leaf movement constraint; and
    e) modifying the apertures generated in step d) by reducing segmentation errors using a network model having nodes corresponding to rows of each aperture in the segmentations generated in step d) and positions of leaves in each row of each aperture to modify one aperture at a time.

2. The method as recited in claim 1 in which step c) includes determining a shortest path of the network model.

3. The method as recited in claim 1 in which the minimization of total leaf movement in step d) is also subject to an interdigitation constraint.

4. The method as recited in claim 1 in which step e) includes calculating a row-non-convexity measure for each of a plurality of intensity maps defined by the apertures in the plurality of segmentations generated in step a), and using the calculated row-non-convexity measure to determine an order in which apertures generated in step d) are to be processed while reducing the segmentation errors.

5. The method as recited in claim 4 in which the row-non-convexity measure includes a measure of a minimum relative segmentation error over a set of apertures in a given segmentation.

6. The method as recited in claim 5 in which the row-non-convexity measure includes a difference between a constrained solution to the minimum relative segmentation error and an unconstrained solution to the minimum relative segmentation error.

7. The method as recited in claim 6 in which the constrained solution is constrained by a single-interval constraint.

8. An intensity modulated arc therapy system comprising:
    a rotatable gantry;
    a radiation source coupled to the rotatable gantry and configured to rotate the radiation source about a target volume through a plurality of delivery angles;

a processor configured to:
  generate a plurality of segmentations, each segmentation defining an intensity of radiation to be delivered from the radiation source to the target volume at one of the plurality of delivery angles;
  order apertures within each of the plurality of segmentations by minimizing total leaf movement between pairs of segmentations in adjacent angles, and thereby calculate corresponding minimum total leaf movement values between such pairs of segmentations;
  select from the plurality of segmentations, a segmentation to be used at each of the plurality of delivery angles of the radiation source using the calculated minimum total leaf movement values and a segmentation selection network model having nodes that each correspond to both the plurality of delivery angles and the plurality of segmentations;
  generate apertures from the selected segmentations by minimizing total leaf movement relative to the selected segmentations subject to a maximum leaf movement constraint;
  produce a radiation delivery plan by modifying the generated apertures by reducing segmentation errors one aperture at a time using a network model having nodes corresponding to rows of each aperture in the generated segmentations and positions of leaves in each row of each aperture; and
  direct the rotatable gantry to rotate about the target volume and to direct the radiation source to deliver radiation to the target volume at each delivery angle in accordance with the produced radiation delivery plan.

9. The intensity modulated arc therapy system as recited in claim 8 in which the processor is further configured to select segmentations by determining a shortest path of the segmentation selection network model.

10. The intensity modulated arc therapy system as recited in claim 8 in which the processor is further configured to generate the apertures from the selected segmentations by minimizing total leaf movement subject also to an interdigitation constraint.

11. The intensity modulated arc therapy system as recited in claim 8 in which the processor is further configured to minimize segmentation errors by calculating a row-non-convexity measure for each of a plurality of intensity maps that are defined by the apertures in the generated plurality of segmentations and using the calculated row-non-convexity measure to determine an order in which apertures generated from the selected segmentations are to be processed while minimizing the segmentation errors.

12. The intensity modulated arc therapy system as recited in claim 11 in which the row-non-convexity measure includes a measure of a minimum relative segmentation error over a set of apertures in a given segmentation.

13. The intensity modulated arc therapy system as recited in claim 12 in which the row-non-convexity measure includes a difference between a constrained solution to a minimum relative segmentation error problem and an unconstrained solution to a minimum relative segmentation error problem.

14. The intensity modulated arc therapy system as recited in claim 13 in which the constrained solution is constrained by a single-interval constraint.

15. The intensity modulated arc therapy system as recited in claim 8 in which the processor is further configured to re-optimize weights associated with the modified apertures that form a part of the produced radiation delivery plan.

* * * * *